US012806619B2

(12) United States Patent
Kiani et al.

(10) Patent No.: US 12,806,619 B2
(45) Date of Patent: Nov. 24, 2026

(54) DEVICES FOR GENERATING PRE-TEMPLATED INSTANT PARTITIONS

(71) Applicant: ILLUMINA, INC., San Diego, CA (US)

(72) Inventors: Sepehr Kiani, Watertown, MA (US); Corey Alicchio, Watertown, MA (US)

(73) Assignee: Illumina, Inc., San Diego, CA (US)

( * ) Notice: Subject to any disclaimer, the term of this patent is extended or adjusted under 35 U.S.C. 154(b) by 1027 days.

(21) Appl. No.: 17/860,359

(22) Filed: Jul. 8, 2022

(65) Prior Publication Data

US 2023/0008992 A1 Jan. 12, 2023

Related U.S. Application Data

(60) Provisional application No. 63/220,097, filed on Jul. 9, 2021.

(51) Int. Cl.
*B01L 3/00* (2006.01)
*B01F 23/41* (2022.01)
(Continued)

(52) U.S. Cl.
CPC ...... *B01L 3/50273* (2013.01); *B01F 23/4143* (2022.01); *B01F 25/10* (2022.01); *B01F 35/214* (2022.01); *B01F 35/2215* (2022.01); *B01F 35/92* (2022.01); *B01L 7/52* (2013.01); *C12Q 1/6851* (2013.01); *B01F 2035/98* (2022.01); *B01F 2035/99* (2022.01); *B01F 2101/23* (2022.01); *B01F 2215/0481* (2013.01);
(Continued)

(58) Field of Classification Search
CPC ......... B01L 3/50273; B01L 2300/0654; B01L 2300/18; B01L 2400/0439; B01L 7/52; B01F 35/2215; B01F 35/92; B01F 35/214; B01F 23/4243; B01F 25/10; B01F 2035/99; B01F 2035/98; B01F 2101/23; B01F 2215/0481; C12Q 1/6851; B33Y 80/00
USPC .......................................................... 137/808
See application file for complete search history.

(56) References Cited

U.S. PATENT DOCUMENTS 4,202,634 A 5/1980 Kraft et al.
4,305,668 A * 12/1981 Bilbrey .................. B01F 31/00 422/537

(Continued)

FOREIGN PATENT DOCUMENTS

AU 2013203624 A1 5/2013
CN 112410213 A 2/2021

(Continued)

OTHER PUBLICATIONS

Final Office Action for U.S. Appl. No. 17/146,768, dated Mar. 12, 2025, 24 pages.

(Continued)

*Primary Examiner* — Minh Q Le
(74) *Attorney, Agent, or Firm* — Illumina, Inc.

(57) ABSTRACT

The invention provides devices for generating pre-templated instant partitions. The devices may include a shearing mechanism, such as a vortexer, a holder for holding a vessel containing a liquid onto the vortexer, and a temperature control unit for modulating a temperature of the vessel by convection. The invention also provides methods of using such devices to process analyte inside the pre-templated instant partitions.

17 Claims, 6 Drawing Sheets

(51) Int. Cl.

| | |
|---|---|
| ***B01F 25/10*** | (2022.01) |
| ***B01F 35/214*** | (2022.01) |
| ***B01F 35/221*** | (2022.01) |
| ***B01F 35/92*** | (2022.01) |
| ***B01L 7/00*** | (2006.01) |
| ***C12Q 1/6851*** | (2018.01) |
| *B01F 35/90* | (2022.01) |
| *B01F 101/23* | (2022.01) |
| *B33Y 80/00* | (2015.01) |

(52) U.S. Cl.

CPC .................. *B01L 2300/0654* (2013.01); *B01L 2300/0829* (2013.01); *B01L 2300/18* (2013.01); *B01L 2300/1822* (2013.01); *B01L 2400/0439* (2013.01); *B33Y 80/00* (2014.12)

(56) References Cited

U.S. PATENT DOCUMENTS 4,701,415 A 10/1987 Dutton
4,883,644 A 11/1989 Perlman
5,036,989 A 8/1991 Carilli
5,512,439 A 4/1996 Hornes et al.
5,632,388 A 5/1997 Morrison et al.
5,813,759 A 9/1998 Gebrian
6,186,657 B1 2/2001 Fuchsbichler
6,210,891 B1 4/2001 Nyren et al.
6,306,597 B1 10/2001 Macevicz
6,309,833 B1 10/2001 Edman et al.
6,828,100 B1 12/2004 Ronaghi
6,833,246 B2 12/2004 Balasubramanian
6,911,345 B2 6/2005 Quake et al.
7,232,656 B2 6/2007 Balasubramanian et al.
7,296,924 B2 * 11/2007 Czarnek .................. B01F 31/27 366/208
7,339,671 B2 * 3/2008 Peng ...................... G01N 21/51 356/244
7,361,472 B2 4/2008 Yguerabide et al.
7,399,671 B2 * 7/2008 Burgess .............. H10W 20/069 257/E21.507
7,537,897 B2 5/2009 Brenner et al.
7,598,035 B2 10/2009 Macevicz
7,835,871 B2 11/2010 Kain et al.
7,842,457 B2 11/2010 Berka et al.
7,960,120 B2 6/2011 Rigatti et al.
8,012,690 B2 9/2011 Berka et al.
8,629,323 B2 1/2014 Weeks
8,715,934 B2 5/2014 Diehl et al.
8,748,102 B2 6/2014 Berka et al.
8,765,380 B2 7/2014 Berka et al.
9,011,777 B2 4/2015 Beer
9,012,390 B2 4/2015 Holtze et al.
9,085,798 B2 7/2015 Chee
9,260,751 B2 2/2016 Diehl et al.
9,388,465 B2 7/2016 Hindson et al.
9,399,797 B2 7/2016 Hutchison et al.
9,562,837 B2 2/2017 Link
9,567,645 B2 2/2017 Fan et al.
9,567,646 B2 2/2017 Fan et al.
9,580,736 B2 2/2017 Tan et al.
9,598,736 B2 3/2017 Fan et al.
9,637,799 B2 5/2017 Fan et al.
9,650,629 B2 5/2017 Froehlich et al.
9,695,392 B2 * 7/2017 Sherman ................. B01F 31/50
9,695,474 B2 7/2017 GigaGen
9,701,998 B2 7/2017 Hindson et al.
9,708,654 B2 7/2017 Hunicke-Smith et al.
9,783,847 B2 10/2017 Chee
9,951,386 B2 4/2018 Hindson et al.
10,030,267 B2 7/2018 Hindson et al.
10,041,116 B2 8/2018 Hindson et al.
10,131,958 B1 11/2018 Fan et al.
10,151,003 B2 12/2018 Fan et al.
10,155,981 B2 12/2018 Brenner et al.
10,202,628 B2 2/2019 Church et al.
10,208,356 B1 2/2019 Fan et al.
10,221,442 B2 3/2019 Hindson et al.
10,240,192 B2 3/2019 Berka et al.
10,240,197 B1 3/2019 Brenner et al.
10,253,375 B1 4/2019 Fan et al.
10,266,883 B2 4/2019 Chee
10,280,459 B1 5/2019 Brenner et al.
10,285,940 B2 5/2019 Mason et al.
10,329,557 B2 6/2019 Johnson et al.
10,344,329 B2 7/2019 Hindson et al.
10,392,662 B1 8/2019 Brenner et al.
10,400,280 B2 9/2019 Hindson et al.
10,415,030 B2 9/2019 Marshall et al.
10,457,986 B2 10/2019 Hindson et al.
10,501,793 B2 12/2019 Chee
10,533,950 B2 * 1/2020 Herzog .................. G01N 15/06
10,584,381 B2 3/2020 Hindson et al.
10,739,236 B1 * 8/2020 Hopkins .................. G01N 1/38
11,060,149 B2 7/2021 Steelman
11,104,961 B2 8/2021 Fontanez et al.
11,142,791 B2 10/2021 Abate et al.
2002/0132251 A1 9/2002 Shuber
2003/0143599 A1 7/2003 Makarov et al.
2003/0180737 A1 9/2003 Gu et al.
2004/0005585 A1 1/2004 Bi et al.
2005/0051466 A1 3/2005 Carter et al.
2006/0024681 A1 2/2006 Smith et al.
2006/0177836 A1 8/2006 McKernan et al.
2006/0292611 A1 12/2006 Berka et al.
2007/0080316 A1 4/2007 Sauer et al.
2007/0114362 A1 5/2007 Feng et al.
2008/0004436 A1 1/2008 Tawfik
2008/0056059 A1 * 3/2008 Manera ............... B01F 35/2214 366/110
2009/0097948 A1 * 4/2009 Zuppiger ................ B01F 31/22 901/50
2009/0280475 A1 11/2009 Pollack et al.
2011/0009278 A1 1/2011 Kain et al.
2011/0086780 A1 4/2011 Colston, Jr. et al.
2011/0118151 A1 5/2011 Eshoo et al.
2011/0176976 A1 7/2011 Ebi et al.
2011/0301061 A1 * 12/2011 McDaniel ............... B01F 23/41 506/12
2011/0311978 A1 12/2011 Makarewicz, Jr. et al.
2012/0295269 A1 11/2012 Pourahmadi et al.
2012/0316074 A1 12/2012 Saxonov
2013/0115169 A1 5/2013 Lahann et al.
2014/0024020 A1 1/2014 Tanabe
2014/0155295 A1 6/2014 Hindson et al.
2014/0293735 A1 10/2014 Vidakovic et al.
2014/0309795 A1 10/2014 Norton et al.
2015/0133312 A1 5/2015 Bielas et al.
2015/0225777 A1 8/2015 Hindson et al.
2015/0232942 A1 8/2015 Abate et al.
2016/0121325 A1 * 5/2016 Masquelier ......... B01L 3/50273 422/561
2016/0186267 A1 6/2016 So et al.
2016/0250608 A1 9/2016 Anders et al.
2016/0266015 A1 9/2016 Loo et al.
2016/0274103 A1 9/2016 Piloto et al.
2017/0073280 A1 * 3/2017 Jones .................. C06B 21/0075
2017/0165670 A1 6/2017 Harder et al.
2017/0189909 A1 7/2017 Lee et al.
2017/0192030 A1 7/2017 Lapham et al.
2017/0218437 A1 8/2017 Seul et al.
2017/0232417 A1 8/2017 Lebofsky et al.
2017/0255160 A1 9/2017 Numata et al.
2017/0269112 A1 * 9/2017 Gerstel .............. G01N 35/1079
2018/0010105 A1 1/2018 Rogers et al.
2018/0051321 A1 2/2018 Hindson et al.
2018/0119216 A1 5/2018 Jamshidi et al.
2018/0133715 A1 5/2018 Craig et al.
2018/0179553 A1 6/2018 Watson et al.
2018/0216162 A1 8/2018 Belhocine et al.
2018/0237836 A1 8/2018 Abate et al.
2018/0274027 A1 9/2018 Hindson et al.
2018/0340880 A1 11/2018 Matsumoto et al.
2018/0355407 A1 12/2018 Utharala et al.

(56) References Cited

U.S. PATENT DOCUMENTS

| | | | | |
|---|---|---|---|---|
| 2019/0030539 | A1 | 1/2019 | Vermaas et al. | |
| 2019/0085412 | A1 | 3/2019 | Fan et al. | |
| 2019/0153532 | A1 | 5/2019 | Bharadwaj et al. | |
| 2019/0153550 | A1 | 5/2019 | Steinmetzer et al. | |
| 2019/0177789 | A1 | 6/2019 | Hindson et al. | |
| 2019/0323003 | A1 | 10/2019 | Ramji et al. | |
| 2019/0323091 | A1 | 10/2019 | Bramlett et al. | |
| 2019/0352714 | A1 | 11/2019 | Salk et al. | |
| 2019/0381497 | A1 | 12/2019 | Di Carlo et al. | |
| 2019/0382753 | A1 | 12/2019 | Steemers et al. | |
| 2020/0040385 | A1 | 2/2020 | Beechem et al. | |
| 2020/0061618 | A1* | 2/2020 | Lee | B01L 3/502769 |
| 2020/0080112 | A1 | 3/2020 | Zhang et al. | |
| 2020/0190513 | A1 | 6/2020 | Fernandez et al. | |
| 2020/0261879 | A1 | 8/2020 | Abate et al. | |
| 2020/0324287 | A1 | 10/2020 | Vijayan et al. | |
| 2020/0376488 | A1 | 12/2020 | Wu et al. | |
| 2021/0010070 | A1 | 1/2021 | Schnall-Levin et al. | |
| 2021/0054369 | A1 | 2/2021 | Meltzer et al. | |
| 2021/0214721 | A1 | 7/2021 | Fontanez et al. | |
| 2021/0214763 | A1 | 7/2021 | Fontanez et al. | |
| 2021/0214769 | A1 | 7/2021 | Fontanez et al. | |
| 2021/0214792 | A1 | 7/2021 | Fontanez et al. | |
| 2021/0214802 | A1 | 7/2021 | Fontanez et al. | |
| 2021/0215591 | A1 | 7/2021 | Fontanez et al. | |
| 2021/0291185 | A1* | 9/2021 | Lee | B01L 3/502761 |
| 2021/0301354 | A1 | 9/2021 | Kiani | |
| 2021/0332432 | A1 | 10/2021 | Kiani | |
| 2021/0340596 | A1 | 11/2021 | Meltzer et al. | |
| 2021/0381064 | A1 | 12/2021 | Fontanez et al. | |
| 2021/0395663 | A1* | 12/2021 | Zhang | C12M 23/50 |
| 2022/0017892 | A1 | 1/2022 | Meltzer et al. | |
| 2022/0099675 | A1* | 3/2022 | Chen | G01N 33/56983 |
| 2022/0135966 | A1 | 5/2022 | Meltzer | |
| 2022/0136071 | A1 | 5/2022 | Meltzer | |
| 2022/0143615 | A1* | 5/2022 | Medoro | G01N 1/40 |
| 2022/0154248 | A1 | 5/2022 | Abate et al. | |
| 2022/0234043 | A1* | 7/2022 | Tanabe | C12N 5/0696 |
| 2022/0235416 | A1 | 7/2022 | Fontanez et al. | |
| 2022/0267761 | A1 | 8/2022 | Fontanez et al. | |

FOREIGN PATENT DOCUMENTS

| | | | |
|---|---|---|---|
| CN | 113274927 | A | 8/2021 |
| EP | 1877170 | B1 | 6/2010 |
| EP | 3819637 | A1 | 5/2021 |
| JP | 2021072863 | A | 5/2021 |
| WO | 1997/008547 | A1 | 3/1997 |
| WO | WO-2009114619 | A1 | 9/2009 |
| WO | 2010/117620 | A2 | 10/2010 |
| WO | 2011/047307 | A1 | 4/2011 |
| WO | WO-2011156084 | A1 | 12/2011 |
| WO | 2012/116146 | A1 | 8/2012 |
| WO | 2012/149042 | A2 | 11/2012 |
| WO | 2013/165748 | A1 | 11/2013 |
| WO | 2014/028537 | A1 | 2/2014 |
| WO | 2014/100434 | A1 | 6/2014 |
| WO | 2014/146025 | A1 | 9/2014 |
| WO | 2014/153071 | A1 | 9/2014 |
| WO | 2015/157369 | A1 | 10/2015 |
| WO | 2015/187792 | A1 | 12/2015 |
| WO | 2016/025815 | A1 | 2/2016 |
| WO | 2016/040476 | A1 | 3/2016 |
| WO | 2016/126871 | A2 | 8/2016 |
| WO | 2016/138080 | A1 | 9/2016 |
| WO | 2016/172373 | A1 | 10/2016 |
| WO | 2017/161306 | A1 | 9/2017 |
| WO | WO-2017201451 | A1 | 11/2017 |
| WO | 2019/011971 | A1 | 1/2019 |
| WO | 2019/023627 | A1 | 1/2019 |
| WO | 2019050840 | A1 | 3/2019 |
| WO | 2019/139650 | A2 | 7/2019 |
| WO | 2019/157529 | A1 | 8/2019 |
| WO | 2019/204229 | A1 | 10/2019 |
| WO | 2019/217552 | A1 | 11/2019 |
| WO | 2019/222523 | A2 | 11/2019 |
| WO | 2020/037214 | A1 | 2/2020 |
| WO | 2020/069268 | A1 | 4/2020 |
| WO | 2020/069298 | A1 | 4/2020 |
| WO | WO-2020156879 | A1 | 8/2020 |
| WO | 2021146171 | A1 | 7/2021 |

OTHER PUBLICATIONS

International Patent Application No. PCT/US2021/013042, filed Jan. 12, 2021, International Search Report and Written Opinion, issued Mar. 29, 2021, 12 Pages.

International Patent Application No. PCT/US2021/013048, filed Jan. 12, 2021, International Search Report and Written Opinion, issued Mar. 31, 2021, 18 Pages.

International Patent Application No. PCT/US2021/013065, filed Jan. 12, 2021, International Search Report and Written Opinion issued Mar. 29, 2021, 15 pages.

International Patent Application No. PCT/US2021/013066, filed Jan. 12, 2021, International Search Report and Written Opinion, issued Mar. 29, 2021, 13 Pages.

International Patent Application No. PCT/US2021/013069, filed Jan. 12, 2021, International Search Report and Written Opinion issued Apr. 1, 2021, 13 Pages.

International Patent Application No. PCT/US2021/022503, filed Mar. 16, 2021, International Search Report and Written Opinion, issued Aug. 11, 2021, 12 Pages.

International Search Report and Written Opinion for International Application No. PCT/US2020/47214, mailed Feb. 3, 2021, 19 Pages.

International Search Report and Written Opinion for International Application No. PCT/US2021/013045, mailed Mar. 29, 2021, 10 Pages.

International Search Report and Written Opinion for International Application No. PCT/US2021/023815, mailed Jun. 30, 2021, 19 Pages.

International Search Report and Written Opinion for International Application No. PCT/US2022/048785, Mar. 17, 2023, 9 pages.

Non-Final Office Action for U.S. Appl. No. 17/146,986, dated Mar. 11, 2021, 7 Pages.

Berensmeier, 2006, Magnetic particles for the separation and purification of necleic acids, Applied Microbiology and Biotechnology, 73:495-504.

Biocompare, 2013, How to maintain a constant temp in your CO2 incubator, Biocompare Life Sciences Articles (7 pages), retrieved from <URL: https://www.biocompare.com/Editorial-Articles/126328-Incubators/#:~text=A jacket of water circulates, thermal buffer against outside air.>.

Bowman, 2013, Multiplexed Illumina sequencing libraries from picogram quantities of DNA, BMC Genomics 14:466 (8 pages).

Brouzes, 2009, Droplet microfluidic technology for single-cell high-throughput screening, Proc Natl Acad Sci 106(34):14195-14200.

Cai, 2019, Selection of DNA-encoded libraries to protein targets within and on living cells, Journal of the American Chemical Society, 141(43):1-11.

Cheng, 2020, Ultra-senstive and rapid detection of nucleic acids and microorganisms in body fluids using single molecule tethering, Nature Communications, 11(1):1-9.

Datlinger, 2017, Pooled CRISPR screening with single-cell transcriptome readout, Nature Methods 4(3):297-301.

Eastburn, 2013, Ultrahigh-trhoughput mammalian single-cell reverse-transcriptase polymerase chain reaction in microfluidic drops, Anal Chem 85:8016-8021.

Fan, 2017, Barcode Doublets, JEFWorksLab (5 pages).

Figueiredo, 2007, Cost effective method for construction of high quality cDNA libraries, Biomol Eng 24:419-421.

Fu, 2015, Uniform and accurate single-cell sequencing based on emulsion whole-genome amplification, PNAS 112(38):11923-11928.

Hatori, 2019, Particle-templated emulsification for microfluidics-free digital biology, Analytical Chemistry, 90:9813-9820.

(56) References Cited

OTHER PUBLICATIONS

High containment laboratories at CDC—Fifty Years of Excellence, Centers for Disease Control and Prevention, retreived from the internet, <https://www.cdc.gov/ncezid/dhcpp/hcl-50/high-containment-laboratories.html>, 1 page.
International Search Report and Written Opinion issued in International Application No. PC/TUS2022/37078, date of mailing: Oct. 12, 2022, 22 pages.
International Search Report and Written Opinion issued in International Application No. PCT/US2022/37129, date of mailing: Oct. 11, 2022, 17 pages.
Jacobsen, 2004, Direct isolation of poly(A)+ RNA from 4 M guanidine thiocyanate-lysed cell extracts using locked nucleic acid-oligo(T) capture, Nucleic Acids Research, 32(7), 10 pages.
Karlsson, 2016, Counting Molecules in cell-free DNA and single cells RNA, Thesis, Division of Molecular Neurobiology Department of Medical Biochemistry and Biophysics, Karolinska Institutet, 51 pages.
Kim, 2018, Single-Cell RT-PCR in microfluidic droplets with integrated chemical lysis, Anal Chem 90(2):1273-1279.
Klein, 2015, Droplet barcoding for single cell transcriptomics applied to embryonic stem cells, Cells, 161(5):1187-1201.
Kukurba, 2015, RNA Sequencing and Analysis, Cold Spring Harb Protoc 11:951-969.
Kumaresan, 2008, High-throughput single copy DNA amplification and cell analysis in engineered nanoliter droplets, Anal Chem, 80:3522-3529.
Kumari, 2017, Quantification of Circulating Free DNA as a Diagnostic Marker in Gall Bladder Cancer, Pathology & Oncology Research, 23:91-97.
Lage, 2003, Whole genome analysis of genetic alterations in small DNA samples using hyperbranched strand displacement amplification and array-CGH, Genome Res 13:294-307.
Lyons, 2017, Large-scale DNA barcode library generation for biomolecule identification in high-throughput screens, Sci Rep 7:13899 (7 pages).
Markus, 2021, Analysis of recurrently protected genomic regions in cell-free DNA found in urine, Science Translational Medicine, 13(581):1-31.
Mazutis, 2013, Singl-cell analysis and sorting using droplet-based microfluidics, Nature Protocols, 8(5):870-891.
Nishikawa, 2015, Monodisperse picoliter droplets for low-bias and contamination-free reactions in single-cell whole genome amplification, PLoSOne 10(9):e0138733 (15 pages).
Patel, 2019, Design and fabrication of low cost vortex mixer using additive manufacturing, International Journal of Applied Engineering Research 14(1):246-249.
Petersen, 2021, Screening of DNA-encoded small molecule libraries inside a living cell, Journal of the American Chemical Society, 143(7):2751-2756.
Quail, 2012, A tale of three next generation sequencing platforms: comparison of Ion Torrent, Pacific Biosciences and Ilumina MiSeq sequencers, BMC Genomics 13:341, 13 pages.
Replogle, 2020, Combinatorial single-cell CRISPR screens by direct guide RNA capture and targeted sequencing, Nat. Biotechnol. 38(8):954-961.
Roche, 2011, emPCR amplification method manual, 454 Life Sciences Corp (12 pages).
Sidore, 2016, Enhanced sequencing coverage with digital droplet multiple displacement amplification, Nucl Acids Res 44(7):e66 (9 pages).
Stoeckius, 2017, Large-scale simultaneous measurements of epitopes and transcriptomes in single cells, Nat Methods 14(9):865-868.
Stoeckius, 2017, Simultaneous epitope and transcriptome measurment in single cells, Nat Meth online pub (10 pages).
Suh, 2012, Synthesis of magnetic hydrogel microparticles for bioassays and tweezer manipulation in microwells, Microfluid Nanofluid, 13:655-674.
Tamminen, 2015, Single gene-based distinction of individual microbial genomes from a mixed population of microbial cells Front Microb 6:195 (10 pages).
Tokunaga, 2013, Systematic exploration of lipophilic tags that allow efficient anchoring of aptamers to live cell surfaces, Chem Lett 42(2):127-129.
Vitale, 2019, An optimized workflow to evaluate estrogen receptor gene mutations in small amounts of cell-fee DNA, The Journal of Molecular Diagnostics, 21(1):123-127.
Walls, 2020, Structure, Function, and Antigenicity of the SARS-CoV-2 Spike Glcoprotein, Cell, 181(2):281-292.
Zilionis, 2016, Single-cell barcoding and sequencing using droplet microfluidics, Natutre Prot 12(1):44-73.
Extended European Search Report dated Oct. 2, 2025, European Patent Application No. 22838457.4, 18 pages.

* cited by examiner

DEVICES FOR GENERATING PRE-TEMPLATED INSTANT PARTITIONS

TECHNICAL FIELD

The invention relates generally to devices and methods for preparing biological samples.

BACKGROUND

Early detection is a major barrier to successful treatment of many diseases. For example, cancer results from genomic changes in single cells. Those changes allow the cells to rapidly proliferate and invade other tissues. In early stages, however, the genetically altered cells represent only a tiny fraction of the cells in a particular tissue or population and can be more easily eradicated if detected early.

To facilitate early detection of cancer, microfluidic systems that allow isolation and analysis of individual cells have been developed. Unfortunately, the use of microfluidic devices requires specialized hardware and highly technical skills. As such, microfluidic systems are simply not cost-effective for most research or clinical facilities. Consequently, each year millions of cases of early-stage diseases continue to go undetected while the window of opportunity for successfully treating those diseases narrows substantially.

SUMMARY

This invention provides devices for separating and processing cells with pre-templated instant partitions. Consequently, devices of the invention are useful to facilitate clinical diagnostic workflows by detecting aberrant cells or molecules present in low quantities, such as tumorigenic cells at early stages of cancer. Specifically, the invention provides devices and methods for producing numerous pre-templated instant partitions in a single vessel from a bulk sample, such as a sample containing millions of cells. The pre-templated instant partitions are formed by shearing liquids within the vessel causing the near instantaneous self-assembly of uniformly-sized droplets. The droplets are formed around template particles that serve as templates for the droplets and facilitate the segregation of single analytes inside the droplets for processing. Each droplet functions as an individual "reaction chamber" which allows for the simultaneous processing of a large number of cells or cellular material on a massively parallel scale. Cells or cellular material are processed using convective heat transfer, which allows for very rapid temperature changes. By controlling the temperature of the pre-templated instant partitions, reactions, such as nucleic acid amplification, reverse transcription, and sequencing, can be independently performed on vast numbers of samples simultaneously.

Devices of the invention include a shearing mechanism, such as a vortexer, coupled to a vessel holder and a temperature control unit. When a vessel containing a liquid, i.e., a mixture of an aqueous solution and oil, with analyte is placed in the holder, the device applies a shearing energy to the liquid. By controlled shear force, the device generates an emulsion of essentially monodisperse droplets (pre-templated instant partitions).

By generating pre-templated instant partitions, devices of the invention allow for the isolation of individual targets, such as single cells or molecules, from bulk biological samples. For example, millions of individual target cells can be captured in separate fluid partitions in an emulsion contained in a single reaction vessel. The droplets function as individual micro-reactors for performing sample preparation steps, such as PCR. Thus, the devices can perform large-scale parallel processing of single target cells or molecules in a bulk liquid.

The devices of the invention have numerous advantages. For example, most conventional microfluidic systems require prefabricated microfluidic chips and sophisticated micropneumatic systems. The microfluidic chips are costly to produce and cannot be readily adapted to change production scale. Moreover, the setup and use of microfluidic systems require substantial training. In contrast, devices of the invention can be used with standard microcentrifuge tubes, such as 0.5 milliliter microcentrifuge tubes, or assay plates, and their use does not require extensive setup, maintenance, or technical training. In fact, devices of the invention can accommodate tubes of different shapes or sizes, which is useful for integrating the devices into existing molecular biology workflows.

Because the devices provided herein include an integrated shearing mechanism, e.g., a vortexer, and a rapid temperature control mechanism, they also are easier to use than prior vortexers for generating pre-templated instant partitions and are also useful to automate many library preparation steps. When immiscible liquids are mixed using other commercially available vortexers, the extent to which pre-templated instant partitions are formed is not adequately controlled. Insufficient mixing results in partitions that are heterogeneous in size, while excessive mixing exposes the biological contents of the liquid partitions to unnecessary force that may cause damage. In both instances, downstream library preparation is negatively impacted. Moreover, because the devices include a temperature control unit (e.g., a convective thermocycler), devices of the invention can perform certain library preparation steps, rapidly, and without any human intervention. This is useful to reduce sample preparation time and minimize opportunities for human error.

Moreover, the temperature control unit operates under principles of convection. As such, the temperature control unit is operable to rapidly change temperatures of sample inside the vessel during sample preparation. In fact, the speed at which sample temperature changes can occur reduces the length of time of certain reactions. This is useful to prepare samples more quickly while minimizing opportunities of sample degradation, such as mRNA decay. Devices of the invention can be used to automate certain library preparation methods, such as lysing single cells segregated inside individual partitions, target capture of analyte (e.g., RNA, DNA, or protein) with capture probes inside the partitions, PCR, cDNA synthesis, etc. Because the library preparations can be automated, chances of human error are substantially reduced.

In preferred embodiments, the temperature control unit operates by forced convection. Forced convection can rapidly change sample temperature and thereby drive enzymatic reactions by quickly supplying, e.g., with a pump or fan, a fluid of a predetermined temperature to a holder securing the vessel. By using forced convection, devices of the invention can process samples more quickly, more precisely, and expend less energy in the process, thereby saving costs. Unlike conventional thermocyclers, which must wait for heating blocks to be heated or cooled to regulate sample temperature, devices of the invention quickly transfer heat to and from the sample by forced fluid movement. By employing forced convection, devices of the invention can process analyte (e.g., capture or amplify nucleic acid), at least 25 percent more quickly.

In one aspect, the invention provides a device for generating pre-templated instant partitions. The device includes a shearing mechanism, i.e., a vortexer, for shearing a liquid contained in at least one vessel. The liquid generally includes a mixture of an aqueous solution comprising analyte (e.g., cells), which is overlaid with oil. Upon shearing the liquid, the liquid divides into a plurality of partitions, near instantaneously, wherein a substantial portion of the plurality of partitions includes one or zero analyte.

Devices of the invention include a holder for securing at least one vessel to the vortexer. Preferably, the holder is designed to accommodate one or more vessels of different shapes and sizes. For example, in preferred embodiments the holder is a clamp. As such, the holder can secure any number or any type of vessel, such as, one or more tubes (e.g., a 0.5 milliliter microcentrifuge tube), a strip of tubes (e.g., a strip of 2, 3, 4, 6, 8, 10, 12, or more tubes), a 15 milliliter conical tube, or a multiwell plate (e.g., a plate with 2, 4, 6, 8, 12, 24, 48, 96, 192, 384, or more wells), which is useful for high-throughput applications.

Devices of the invention further include a temperature control unit. The temperature control unit preferably operates by forced convection, in which fluid is forced through conduits within the device to transfer and remove heat from a vessel contained in the holder. The temperature control unit can rapidly and precisely change a temperature of a sample inside the vessel by supplying fluid of a predetermined temperature, which is useful for processing analyte within the plurality of partitions. Accordingly, devices of the invention are useful to generate pre-templated instant partitions and process analyte inside those partitions by rapidly vortexing a vessel containing analyte inside a liquid, and rapidly regulating temperatures inside the vessel to orchestrate various reactions, such as, cell lysis and target capture or PCR.

In order to facilitate sample partitioning, devices of the invention are operable to vortex vessels at high speeds. For example, devices of the invention can achieve vortex speeds of up to about 5,000 revolutions per minute. Moreover, devices of the invention allow for vortexing to be carried out while the vessel is held in one or more different positions, which is useful to achieve adequate mixing of samples. For example, devices of the invention may include a holder that is operable to hold at least one vessel in a substantially vertical position when shearing the liquid. The holder can also hold the sample in a substantially horizontal position when shearing the liquid. Or, the holder can alternate between at least two different positions. For example, the holder can hold the vessel in a substantially horizontal position and then in a substantially vertical position, or vice versa, at different timepoints while shearing the liquid.

Standard thermomixers are generally isothermal. They may have a custom machined block with a heater attached to heat and cool through conduction. However, this does not allow for rapid changes in temperature necessary for performing many PCR, or other molecular biology reactions, that are sensitive to temperature transitions. Conversely, devices of the invention include a temperature control unit that can regulate temperatures of partitions, and thus the reactions therein, using forced convection. This dramatically changes the amount of time it takes to transfer heat, especially with the addition of concurrent sample mixing which further improves heat transfer. This process allows for shorter PCR cycles for ePCR (which are 2-6 times longer than standard PCR cycles) since the speeds that devices of the invention are able to heat and cool are an order of magnitude faster than any conventional thermomixer. This rapid and precise temperature cycling enables, among other things, controlled cell lysis and target (e.g., RNA, DNA, protein) capture, for example, with capture probes attached to template particles. In some applications, PCR in pre-templated instant partitions is desirable (dPCR, for example). Rapid thermal cycling may permit integrated emulsion and PCR on the same instrument.

In preferred embodiments, devices of the invention include a temperature control unit having one or more conduits through which fluid is forced. The fluid can be heated or cooled to a preselected temperature within the one or more conduits. For example, the temperature control unit may include a first conduit for heating the fluid to first temperature. The fluid may be selectively heated to the first temperature by passing the fluid through the first conduit. After passing the fluid through the first conduit, the fluid can be flowed, via a pump or fan, towards the holder to thereby heat a sample contained therein. The temperature control unit can also include a second conduit for cooling the fluid to a second temperature. By passing the fluid through the second conduit, the fluid can be selectively cooled to the second temperature. During sample processing, sample temperature can be managed by alternating fluid flow between the first conduit and the second conduit, thereby heating and cooling the fluid, respectively. By alternating fluid flow between the conduits, the temperature of the sample inside the vessel can be cycled.

For example, the first conduit can heat a fluid (e.g., air) to a first temperature (e.g., >90 degrees Celsius). After, or coincident with, shearing a liquid inside a vessel with the device, fluid of the first temperature can be supplied to an area near or in contact with a vessel containing partitions to lyse single cells contained inside those partitions. After cell lysis, the flow of the fluid may be redirected, for example, by changing a position of a valve, to direct the fluid through the second conduit. Flowing the fluid through the second conduit results in the fluid being rapidly cooled to a second temperature (e.g., <80 degrees Celsius), which is subsequently supplied to the area near or in contact with the vessel to thereby cool the sample temperature and cause the capture of analyte released from the single cells.

In some embodiments, devices of the invention further include an optical system to monitor formation of pre-templated instant partitions and/or monitor reactions that are carried out therein. Accordingly, unlike conventional thermomixers which are a “black box” and do not allow for visual inspection of products during production processes, devices of the invention provide for an optical system to visualize and monitor quality throughout one or more library preparation steps. The optical system may include one or more light sources and one or more photodetectors. Each light source may be positioned to transmit light into the liquid in a vessel. Each light source may be positioned to transmit light to the liquid in a different well of a vessel. Each photodetector may be positioned to sense the transmitted light (e.g., light scatter) from the liquid in a different vessel. Each photodetector may be positioned to sense the transmitted light from the liquid in a different well of a vessel. The light source may be from a laser, a light emitting diode, or from a lamp, such as, mercury arc lamp.

Devices of the invention may further include a control system. The control system may be coupled to the vortexer and the optical system. The control system may control the speed of the vortexer in response to the transmitted light. The control system may increase or decrease the speed of the vortexer. The control system may initiate or stop the vortexer. The control system may direct the vortexer to stop applying a shearing energy to the liquid when the liquid comprises substantially monodisperse droplets.

Moreover, to reduce costs and enhance flexibility for part optimization and manufacturing, devices of the invention include at least one component manufactured by 3D printing. In some instances, the housing or the holder is manufactured by 3D printing. As such, devices of the invention can be quickly and cheaply modified to accommodate different vessel sizes or shapes, which is useful to scale up or scale down library preparation processes. Devices of the invention can use 3D printing to create integrated insulation, i.e., honeycomb infill. Devices of the invention can also use 3D printing to facilitate machine services in the field by quickly and efficiently printing new and replacement parts.

According to another aspect, the invention provides a method for generating pre-templated instant partitions. The method includes contacting at least one vessel containing a liquid with a device comprising a vortexer, a holder to secure at least one vessel to the vortexer, and a temperature control unit in fluidic communication with the holder. The method further includes operating the device to shear the liquid inside at least one vessel into a plurality of pre-templated instant partitions, wherein each of the plurality of pre-templated instant partitions comprise one or zero analyte. For example, operating the device to shear the liquid may involve vortexing the liquid at a speed of 5,000 revolutions per minute.

Methods of the invention are useful to make pre-templated instant partitions and rapidly process sample material inside those partitions. Advantageously, devices of the invention include modules for regulating temperatures quickly and efficiently by forced heat convection. Accordingly, some embodiments of the invention include providing a fluid of a predetermined temperature towards the holder via a first conduit. The first conduit may include a solid-state heating mechanism to rapidly heat the fluid to a first predetermined temperature. Additionally, methods of the invention further include directing the flow of fluid through a second conduit. The second conduit comprises a Peltier to rapidly cool the fluid. The cooled fluid is then flowed towards the holder to cool the sample liquid.

Methods may include operating the device for automated production of pre-templated instant partitions or automating reactions carried out within the partitions. For example, methods of the invention may include transmitting a light to the liquid in at least one vessel and sensing the transmitted light from the liquid in at least one vessel. In some embodiments, methods include comparing the transmitted light from the liquid in at least one vessel to a reference and adjusting the speed of the vortexer in response to the comparison. The method can include comparing the transmitted light from the liquid in at least one vessel to a reference. The reference may be transmitted light from a sample that has not been exposed to a shearing force. The reference may be transmitted light from a sample that has pre-templated instant partitions. The pre-templated instant partitions may have a defined size or range of sizes.

DETAILED DESCRIPTION

Figure 1:
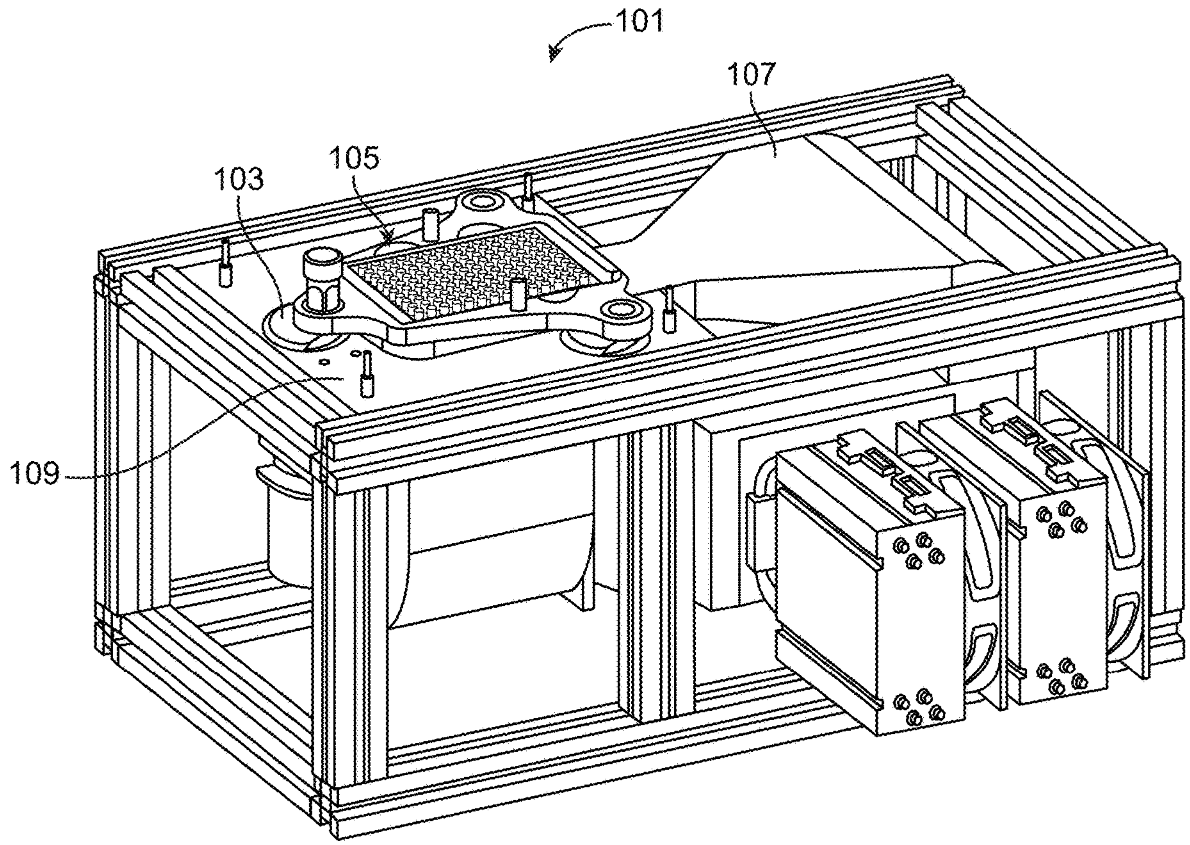
FIG. 1 illustrates an exemplary device for making pre-templated instant partitions.

This invention provides sample preparation instrumentation for generating pre-templated instant partitions of uniform size and for processing analyte inside those partitions. The formation of the pre-templated instant partitions is useful for a variety of research and diagnostic applications because it allows individual targets, such as single cells or single molecules, to be captured inside separate partitions containing a pre-defined volume of liquid for individual processing. The liquid may include reagents for performing various sample processing reactions inside the partitions. By subsequent manipulation of the partitions, reactions, such as nucleic acid amplification, reverse transcription, and sequencing, can be independently performed on vast numbers of samples simultaneously. Consequently, the devices are useful for detection of aberrant cells or molecules that are present in low quantities, such as tumorigenic cells in an early stage of cancer.

Although the utility of reaction cells that contain individual targets has been recognized for years in molecular biology, prior systems for making emulsions of droplets that contain individual targets are problematic. A predicate to obtaining individualized reaction cells is the production of monodisperse, i.e., uniformly sized droplets. Monodisperse droplets can be generated using microfluidic systems, which typically involve controlled injection of two or more liquids into a microfluidic chip having custom-designed fluid channels to permit proper mixing of the liquids. Because the design of a microfluidic system must be optimized to produce droplets of a particular size based on the input liquids, microfluidic chips generally cannot be adapted to produce droplets of different sizes for different applications. In addition, because the chips must be prefabricated but typically cannot be reused, they are costly. Finally, the setup and maintenance of microfluidic pumping systems is not trivial and requires a level of trained expertise. Devices described herein avoid those pitfalls.

Devices permit manufacture of pre-templated instant partitions from bulk liquid (a liquid containing millions or more analyte, e.g., cells) in simple vessels, such as test tubes or multiwell plates, so they do not require specialized disposable supplies. In addition, because droplet size and contents are determined by the size of particles, discussed in detail below, added to the liquid, the devices can be readily adapted to produce droplets having different properties by altering the content of the input particles. Moreover, the devices are simple to use and do not require extensive cleaning or maintenance between uses.

In addition, devices of the invention are useful to perform certain laboratory preparation steps by rapidly, and precisely, changing sample temperature. To facilitate rapid changes in temperature, devices of the invention generally include a convection-based temperature control unit that is operable to rapidly change temperatures of an environment where the vessel is secured during sample preparation. For example, the temperature control apparatus can be used to raise or lower the temperature by programming the device with instructions via an interface operable to receive user input. Devices of the invention can be used to automate certain library preparation methods, such as lysing single cells segregated inside individual partitions, target capture of analyte (e.g., RNA, DNA, or protein) with capture probes inside the partitions, PCR, qPCR, digital PCR, cDNA synthesis, etc. Because the library preparation steps can be pre-programmed for automated processing, devices of the invention substantially reduce opportunities for human error.

In preferred embodiments, the temperature control unit controls sample temperature by thermal convection. Convection, or convection heat transfer, involves the transfer of heat by the movement of fluid, such as air or water. When fluid is caused to move away from a source of heat, e.g., a heater, thermal energy is carried with it. The convection-based temperature control unit is useful to rapidly adjust a temperature of the vessel by quickly moving fluid of predetermined temperatures to and away from the vessel. Moreover, because portions of the fluid can be maintained at a desired temperature inside one or more conduits that are separate from the sample holder, the temperature of the vessel, and thus the sample therein, can be changed quickly and effectively by forcing (e.g., pumping) the fluid, which can be preheated to the desired temperature, to the holder. Accordingly, unlike conventional thermocyclers, devices of the invention do not need to wait for heating blocks to be heated or cooled to regulate sample temperature.

FIG. 1 illustrates an exemplary device 101 for making pre-templated instant partitions. The device 101 includes a vortexer 103 for shearing a liquid contained in at least one vessel. The device 101 also includes a holder 105 for securing at least one vessel to the vortexer 103. The device further includes a temperature control unit 107 to rapidly change the temperature of a sample in at least one vessel. In particular, the temperature control unit 107 manages a temperature of a fluid, by convection. The temperature control unit further manages a flow path of the fluid through the device to control the transfer of heat to or away from the sample.

The holder 105 is designed to secure at least one vessel to a frame 109 of the device 101. The holder 105 can be any device suitable for holding at least one vessel. The holder 105 may be or include a clamp, a platform, a rack, or a tray. Preferably, the holder includes a clamp for easily accommodating vessels of various sizes and shapes. The clamp (not shown) may be integral with the platform, rack, or tray, or it may be separate from the platform, rack, or tray.

The holder 105 can be mounted to a frame 109 such that the holder 105 can accommodate movement, with respect to the frame 109, while shearing the liquid. For example, the holder 105 can be mounted such that the holder 105 can oscillate or swirl in a circular motion, and/or move along one or more of a horizontal or vertical planes while shearing the liquid for the purpose of applying a shearing force to the liquid inside the vessel held by the holder 105.

The shearing force is applied to the sample to generate pre-templated instant partitions in the liquid, which is typically an aqueous liquid having an oil overlay. Optimal generation of pre-templated instant partitions may be achieved by applying a shearing force within a certain range. For example, when the shearing force is inadequate, large droplets that contain multiple partition-templating particles may not be broken into single-particle droplets. On the other hand, excessive shearing force may damage the particles and/or the targets to be captured by the droplets.

In certain embodiments, the shearing force is applied by vortexing or agitating the sample. The sample, while secured in the holder 105, can be vortexed by the actuation of a motor-driven agitator (vortexer) that drives movement of the holder 105 relative to the frame 109. The sample may be vortexed or agitated for a defined period. For example and without limitation, the sample may be vortexed or agitated for about 1 second, about 2 seconds, about 4 seconds, about 6 seconds, about 8 seconds, about 10 seconds, about 15 seconds, about 20 seconds, about 30 seconds, about 45 seconds, about 1 minute, about 2 minutes, about 3 minutes, about 4 minutes, or about 5 minutes. The sample may be vortexed or agitated at a defined speed. For example and without limitation, the sample may be vortexed or agitated at about 5,000 revolutions per minute (rpm), at about 4,000 rpm, at about 3,000 rpm, at about 1,000 rpm, at about 500 rpm, about 600 rpm, about 700 rpm, about 800 rpm, about 900 rpm. In some instances, a vortexing speed above 5,000 rpm may be desired. For the purposes of the disclosure, about means within 15 percent above or below the identified rpm.

The shearing force applied may be above a lower threshold but below an upper threshold. For example, devices of the invention may achieve an adequate shearing force by vortexing the vessel at speeds of up to 6,000 rpm, and above 2,000 rpm. Or, devices of the invention may achieve an adequate shearing force by vortexing at speeds of up to 5,000 rpm and above 3,000 rpm. Preferably, the shearing force is about 5,000 rpm. In addition, devices of the invention can provide relatively slow vortex speeds, e.g., between about 20-100 rpm, such as, 50 rpm, which is useful for thermomixing.

In some embodiments, devices of the invention include an integrated optical system for visualizing the formation of pre-templated instant partitions. The optical system may operate in conjunction with a control system for regulating an amplitude or duration of vortexing. By controlling the duration and amplitude of the shearing force, the device can reliably generate pre-templated instant partitions of similar construct. Once near-uniformity in droplet size is achieved, the optical system can detect a change in the transmitted light. The device may then cease application of shearing force, notify the user, and/or allow subsequent reactions to be performed. For further discussion of optical systems for use with devices herein, see co-owned application Ser. No. 17/146,768, which is incorporated by reference.

Advantageously, devices 101 of the invention include mechanisms for controlling the temperature of a sample inside the one or more vessels, which is useful to control the speed and/or occurrence of various reactions that are carried out within the pre-templated instant partitions. Specifically, in preferred embodiments the device 101 includes a temperature control unit to modulate the temperature of the sample using thermal convection. By using thermal convection, the amount of time it takes to transfer heat to, or remove heat from, the sample can be substantially reduced, thus increasing the rate and efficiency of reactions inside the sample. This is especially useful for processing sensitive samples of low quantity or low abundance. For example, to quickly copy unstable RNA of a single cell into cDNA, which is substantially more stable.

Figure 2:
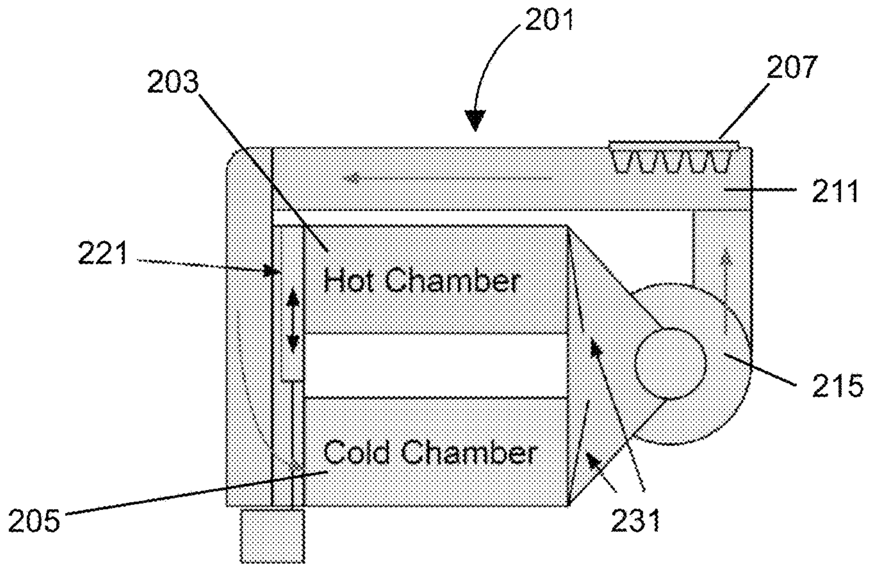
FIG. 2 illustrates an exemplary temperature control unit.

FIG. 2 illustrates an exemplary temperature control unit 201. The temperature control unit 201 includes at least two conduits, also referred to as chambers, for heating or cooling a fluid to a predetermined temperature. The temperature control unit 201 includes a first conduit 203 for heating a fluid (e.g., hot air or water) to a first temperature and a second conduit 205 cooling the fluid to a second temperature. The temperature of the fluids within the conduits is adjustable. Preferably the temperature of the fluid is adjustable by solid-state thermoelectric technology, e.g., Peltier cooling.

Solid-state thermoelectric devices use electricity and semiconductors to produce cooling and heating. As opposed to refrigerants used in conventional cooling systems. The magnitude of heat flow is adjustable by varying the amount of electrical current. Solid-state thermoelectric devices are preferable for several reasons. First, there are no moving parts. This means solid-state thermoelectric technology can provide the devices with higher reliability, which leads to substantial cost savings. Also, unlike compressor based conventional cooling systems, solid-state thermoelectric heating and cooling does not require expensive refrigerants. Accordingly, devices of the invention are more environmentally friendly. By virtue of solid-state technology, systems of the invention can be scaled from less than one watt of cooling power up to kilowatts. The ability to scale thermoelectric thermal management systems offers a much wider range of device configurations. Common components can be used for large- and small-scale devices. This results in reduced manufacturing and design costs.

Devices of the invention can regulate temperature by forced convection. Forced convection involves the forced movement of fluid within the system. The movement of fluid can be forced with a fan or a pump 215. To control sample temperature, the temperature control unit forces fluid through one of at least two conduits. The passing of the fluid through the first conduit 203 causes the fluid to increase in temperature. The fluid increases in temperature by virtue of a heater that is associated with a portion of the conduit. The heater transfers thermal energy into the fluid as the fluid passes through the conduit. The heater is operable to heat the fluid up to about 130 degrees Celsius, for example, up to 110 degrees Celsius, or 100 degrees Celsius, or at least 90 degrees Celsius.

The second conduit 205 can be coupled with a Peltier device, which can transfer thermal energy with consumption of electrical energy to achieve reduced fluid temperatures. For example, the second conduit 205 can provide a fluid temperature of about 0 degrees Celsius. For example, of about 5 degrees Celsius, or 10 degrees Celsius, or 15 degrees Celsius. In some embodiments, a third, fourth, or fifth additional conduit may be provided. The additional conduits may be useful to rapidly supply fluids having temperatures between 0 degrees and 130 degrees Celsius.

The first 203 and second conduit 205 provide fluid of a first or second temperature, respectively, to a sample held by the holder 207 by virtue of being in fluidic communication with an area that is near, or in contact with, the holder 207. The first conduit 203 and second conduit 205 provide fluid towards the holder 207, and thus regulate sample temperature, by virtue of being in fluidic communication with a thermal environment associated with the holder 207. For example, a bottom surface of the holder 207 may be disposed substantially within a fluidic channel 211 of the convection heating apparatus. The bottom surface may comprise a material that is of a low specific heat, and thus sensitive to rapid temperature changes of the fluid. Advantageously, the temperature control unit 201 is configured to control fluid flow through the first conduit 203 and second conduit 205 by a single fan or pump. This is useful for minimizing manufacturing costs.

The temperature control unit 201 includes a mechanism to selectively direct forced fluid flow through the first 203 or the second 205 conduit. By controlling which conduit the forced fluid is flowed through, the temperature of the sample can be regulated. For example, preferably the temperature control unit 201 includes a valve 221, such as a sliding valve, for directing forced fluid flow. The valve 221 can be moved into one of at least two positions. In a first position, the fluid is blocked from flowing into the first conduit 203. This forces the fluid to flow through the second conduit 205, as illustrated by the curved arrowhead. Alternatively, the valve can be moved into a second position, in which fluid flow into the second conduit 205 is blocked. Blocking fluid from flowing into the second conduit 205 causes fluid to move through the first conduit 203, thus heating the fluid. The valve can further be positioned into any number of intermediate positions between the first position and second position, thereby blocking various portions of fluid from flowing through the first 203 and second 205 conduits. This is advantageous since it allows the temperature of the fluid to be quickly changed by heating or cooling various fractions of the total fluid. The temperature control unit 201 further includes self-closing flaps 231 to prevent fluid from flowing back into one of the first or second conduits and also to prevent thermal energy from escaping.

Figure 3:
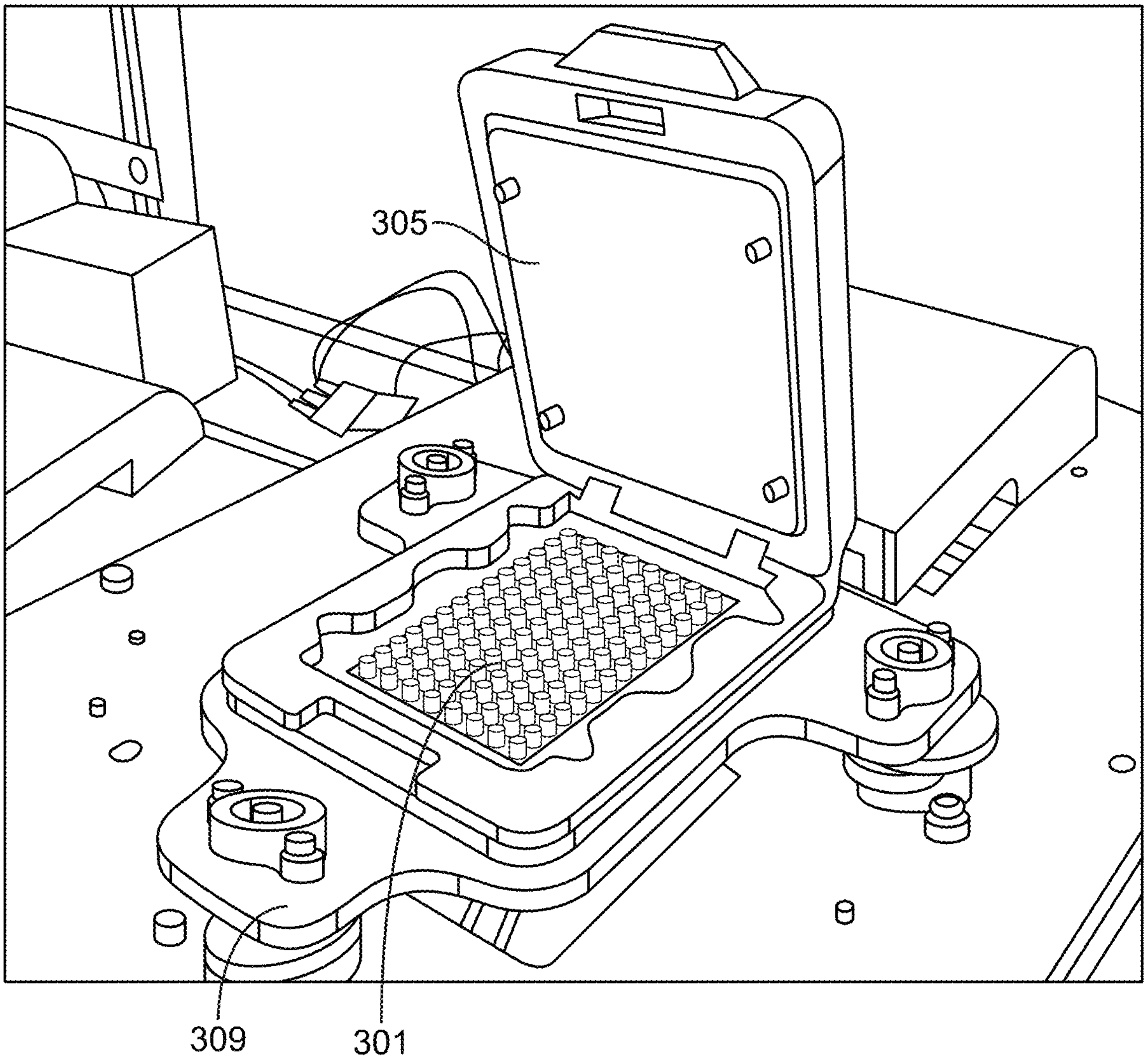
FIG. 3 shows an image of an exemplary holder.

FIG. 3 shows an image of an exemplary holder 301. The holder includes a clamping lid 305 for securing one or more vessels inside the holder. The clamping lid 305 may include a copper spring plate which is useful for heating a top surface of the vessels, thereby ensuring the temperature within the vessel is homogenous. In some embodiments, the claiming lid includes a 30-watt 24 volt membrane heater, which is useful for rapidly changing the temperature of the lid coincident with changes in temperature of the fluid within the temperature control unit 201.

The holder is coupled with a shearing mechanism 309. The shearing mechanism may be any device capable of applying a shearing force to the liquid in the vessel. In some embodiments, the shearing force is applied by moving the holder 301, such as by spinning, rotating, shaking, or rocking the holder 301. In such embodiments, the shearing mechanism may be or include an agitator, shaker, or vortexer. In some embodiments, the shearing force is applied through an electrical force. In such embodiments, the shearing mechanism may be or include a piezoelectric motor. In some embodiments, the shearing force is applied through sound waves. In such embodiments, the shearing mechanism may be or include a sonicator or ultrasonic device. The shearing force may be applied by a combination of means, and the shearing mechanism may be or include any combination of the aforementioned devices.

The holder 301 is designed to hold any vessel or container suitable for holding liquid. For example, and without limitation, the vessel may be a tube or a well in a multiwell plate. The vessel may be or include a set of tubes physically connected to each other. For example, the vessel may be or include a strip of 2, 3, 4, 6, 8, 10, 12, or more tubes. The vessel may be or include a well in plate with 2, 4, 6, 8, 12, 24, 48, 96, 192, 384, or more wells.

To facilitate shearing of the liquid, the holder 301 can hold the least one vessel in either of a substantially vertical position or a substantially horizontal position while shearing the liquid. As such, devices of the invention have the ability to mix horizontally and vertically (asymmetrical mixing), automatically, without physically needing to change the holder or rotate the tubes by hand. This allows for controlled thermo-mixing, which can aid sample distribution in packed templates and accommodate applications where desired thermal incubation is valuable (for example, in emulsion PCR). Shear in samples is enhanced when the axial symmetry of the containing vessel is broken. This can be enabled by holding standard tubes in a horizontal or angled orientation. For example, the holder 301 may be attached to a moveable arm configured to move axially, in any direction, and/or rotate while shearing the liquid. Shearing can also be evoked by changing the tube shape to a non-circular shape or by using a ribbed tube, all of which can be accommodated by flexible tube holders of the device.

Figure 4:
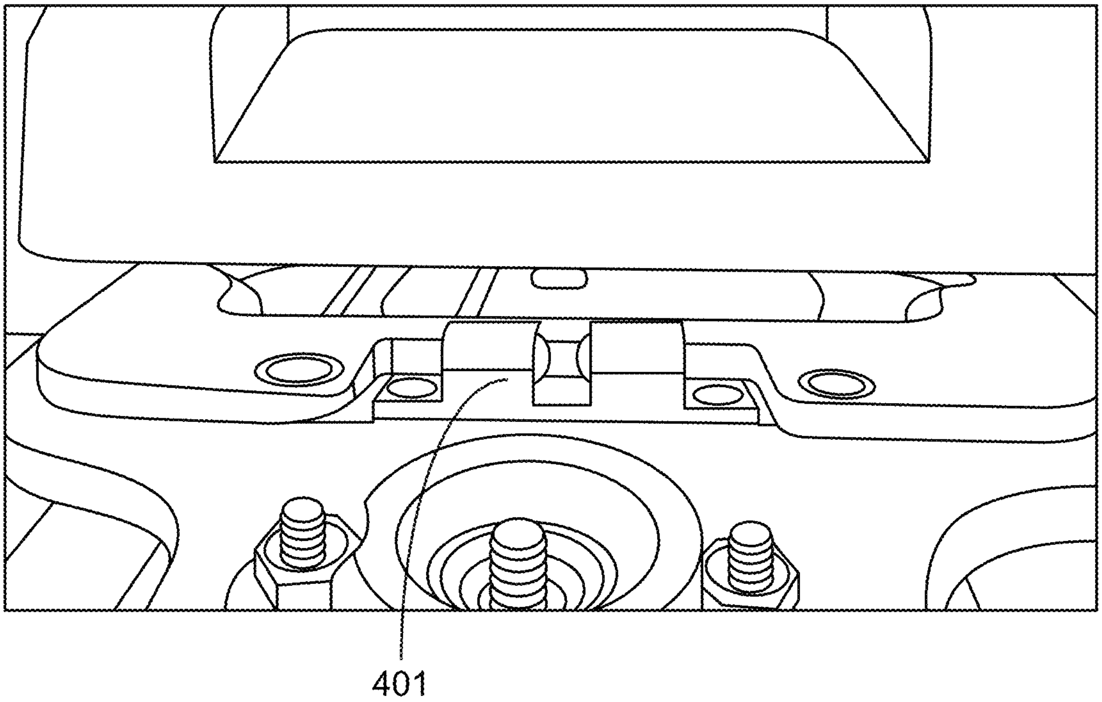
FIG. 4 shows an adjustable latching mechanism.

FIG. 4 shows an adjustable latching mechanism 401. The adjustable latching mechanism allows the holder 301 to accommodate vessels of various sizes or shows. By adjusting the latching mechanism, larger or smaller tubes can be accommodated within devices of the invention.

Figure 5:
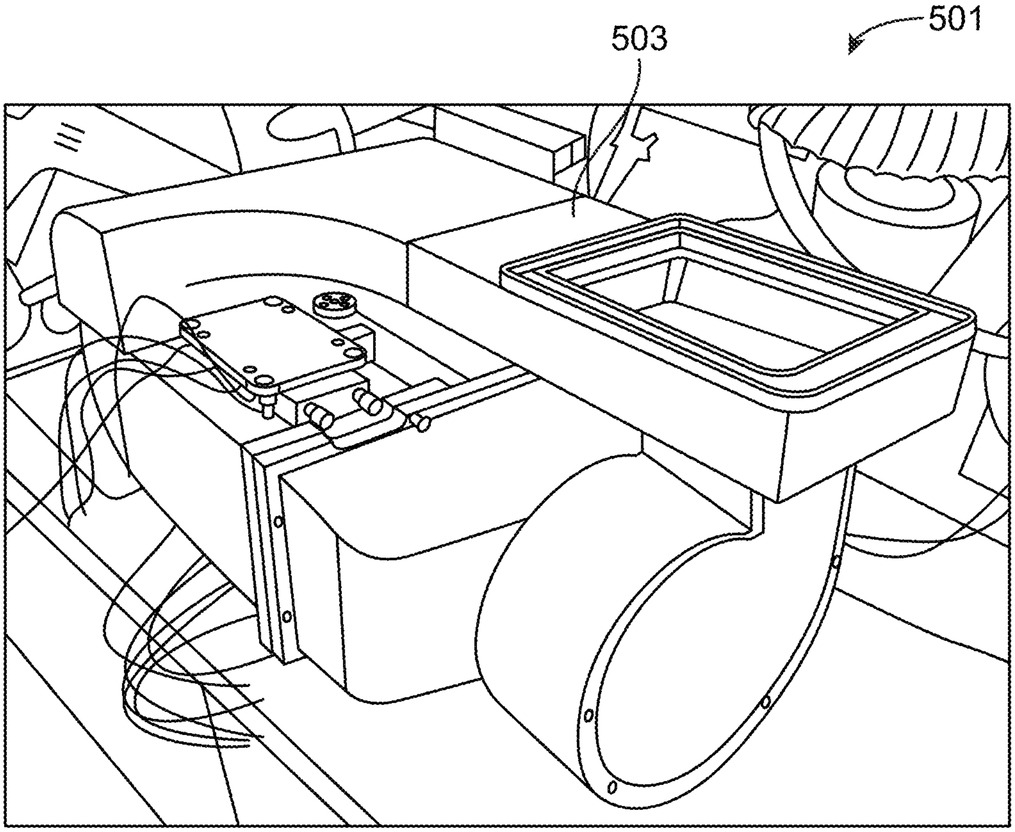
FIG. 5 shows a device according to one embodiment of the invention.

FIG. 5 shows a device 501 according to one embodiment of the invention. The device 501 includes integrated vortexing and thermal controls. To reduce manufacturing costs, at least one component of the device 501 can be manufactured by 3D printing. For example, in some instances the housing 503 is manufactured by 3D printing. The housing 503 can additionally provide insulation for more precise thermoregulation. By implementing 3D printing, costs of manufacture are substantially reduced and flexibility for part optimization is increased. In some instances, 3D printing is used to create integrated insulation, for example, honeycomb infills. 3D printing also provides for the opportunity to service machines in the field by quickly and efficiently printing new and replacement parts.

Figure 6:
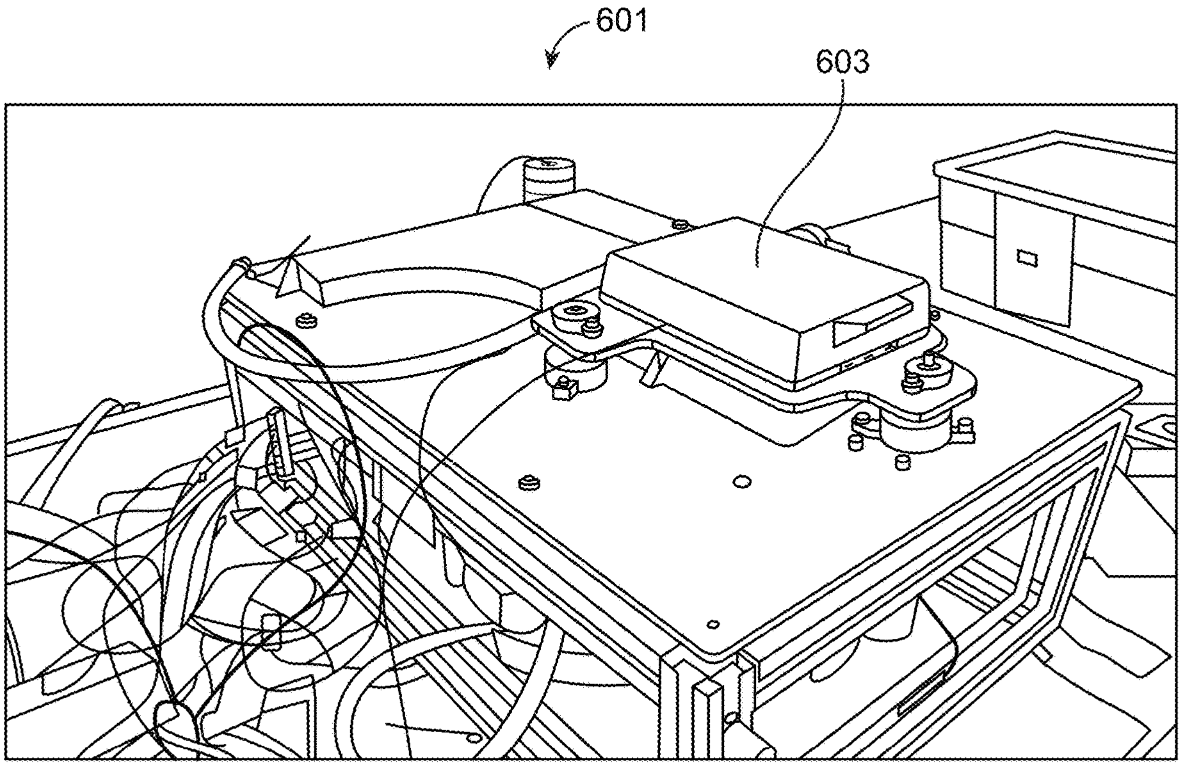
FIG. 6 shows a device for making pre-templated instant partitions according to a different embodiment.

FIG. 6 shows a device 601 for making pre-templated instant partitions according to a different embodiment. The device includes a heated lid involving a clamp 603 for accommodating tubes of various shapes and sizes. For example, the clamp 603 is useful to secure vessels having a non-circular shape, or vessels such as a ribbed tube, both of which are incompatible with conventional thermomixers but are useful for efficiently shearing liquids into partitions.

According to another aspect, the invention provides a method for generating pre-templated instant partitions. The method includes contacting at least one vessel containing a liquid with a device comprising: a vortexer, a holder to secure at least one vessel to the vortexer, and a temperature control unit in fluidic communication with the holder. The method further includes operating the device to shear the liquid inside at least one vessel into a plurality of pre-templated instant partitions, wherein each of the plurality of pre-templated instant partitions comprise one or zero analyte. For example, operating the device to shear the liquid may involve vortexing the liquid at a speed of 5,000 revolutions per minute.

Methods of the invention are useful to make pre-templated instant partitions and rapidly process sample material inside those partitions.

For example, methods of the invention may include performing one or more library steps inside the partitions. For example, in some instances, methods of the invention involve shearing a liquid containing cells, causing single cells to be isolated inside the partitions. The method may further include lysing the single cells inside the partitions. Cell lysis may be induced by heating the holder to a temperature sufficient to cause cell lysis. For example, in some embodiments, lysing involves heating the partitions to a temperature sufficient to release lytic reagents contained inside template particles into the partitions. Advantageously, with devices of the invention, lysis can be rapidly achieved by thermal convection.

In some embodiments, upon lysing the cells inside the partitions, RNA (e.g., mRNA) and or DNA is released from the cells into the partitions for capture with a capture oligos provided by a template particle, as discussed below. The capture oligo can include unique barcodes specific to each template particle. Accordingly, upon capture, i.e., hybridization, of the RNA and/or DNA and a complementary portion of a capture oligos, all of the RNA and/or DNA of single cells are effectively linked by a common barcode sequence. Since each partition includes only one single cell and one template particle, the unique barcode sequences of any one template particle is useful for associating RNA and/or DNA with single cells from which they are released.

Capture is performed by rapidly cooling the temperature of the partitions to a temperature sufficient for hybridization. Because devices of the invention can manage temperature changes by forced convection, the time between temperature cycles is reduced, thus the time between cell lysis and capture is substantially reduced, compared with conventional methods. This reduction in time between cell lysis and capture is significant since it is during this time window that many nucleic acids are degraded or digested by certain factors, such as nucleases. In some instances, temperature changes are automatic. For example, changes in temperature may occur based on instructions inputted into the device by a user. The instructions may be input into the device via an interface of the device.

After capture, methods of the invention may include reverse transcribing captured RNA into cDNA. Reverse transcription can be carried out to generate a library comprising cDNA with barcode sequences that allows each sequence read of a library to be traced back to the single cell from which the mRNA was derived. Once a library is generated comprising barcoded cDNA, the cDNA can be amplified, by for example, PCR, to generate amplicons for sequencing.

According to some embodiments, methods of the invention include operating a device of the invention to perform PCR on DNA contained inside pre-templated instant partitions. Advantageously, devices of the invention modulate temperature using forced air convection. This dramatically changes the amount of time it takes to transfer heat. This allows for shorter PCR cycles since the speeds of heating and cooling are an order of magnitude faster than most thermomixers. For example, using devices of the invention, DNA amplification can occur in approximately one half or one third the amount of time as would be required using a standard thermocycler.

Methods may include operating the device for automated production of pre-templated instant partitions or automating reactions carried out within the partitions. For example, methods of the invention may include transmitting a light to the liquid in at least one vessel and sensing the transmitted light from the liquid in at least one vessel. In some embodiments, methods include comparing the transmitted light from the liquid in at least one vessel to a reference and adjusting the speed of the vortexer in response to the comparison. The method can include comparing the transmitted light from the liquid in at least one vessel to a reference. The reference may be transmitted light from a sample that has not been exposed to a shearing force. The reference may be transmitted light from a sample that has pre-templated instant partitions. The pre-templated instant partitions may have a defined size or range of sizes.

The invention relates to methods of generating pre-templated instant partitions, for example, as discussed in Hatori, 2018, Particle-templated emulsification for microfluidics-free digital biology, Anal Chem 90:9813-9820, which is incorporated by reference. Briefly, an aqueous mixture is prepared in a reaction tube that includes template particles and analyte (e.g., cells or nucleic acid) in aqueous fluid (e.g., water, saline, buffer, nutrient broth, etc.). An immiscible fluid (e.g., oil) is added to the tube, and the tube is agitated. The particles act to template the formation of partitions that each contain one template particle in an aqueous droplet, surrounded by the oil.

The template particles may provide oligonucleotides for target capture and barcoding of analyte, such as DNA or RNA. Barcodes specific to each template particle may be any group of nucleotides or oligonucleotide sequences that are distinguishable from other barcodes within the group. Accordingly, a partition encapsulating a template particle and a single cell, for example, provides to each nucleic acid molecule released from the single cell the same barcode from the group of barcodes. The barcodes provided by template particles are unique to that template particle and distinguishable from the barcodes provided to nucleic acid molecules by every other template particle. Once sequenced, by using the barcode sequence, the nucleic acid molecules can be traced back to the single cell based on the barcode provided by the template particle that the single cell was partitioned with. Barcodes may be of any suitable length sufficient to distinguish the barcode from other barcodes. For example, a barcode may have a length of 4, 5, 6, 7, 8, 9, 10, 11, 12, 13, 14, 15, 16, 17, 18, 19, 20, 21, 22, 23, 24, 25 nucleotides, or more.

In some methods of the invention, an index or barcode sequence may comprise unique molecule identifiers (UMIs). UMIs are advantageous in that they can be used to correct for errors created during amplification, such as amplification bias or incorrect base pairing during amplification. For example, when using UMIs, because every nucleic acid molecule in a sample together with its UMI or UMIs is unique or nearly unique, after amplification and sequencing, molecules with identical sequences may be considered to refer to the same starting nucleic acid molecule, thereby reducing amplification bias.

Template particles may be porous or nonporous. In any suitable embodiment herein, template particles may include microcompartments (also referred to herein as “internal compartment”), which may contain additional components and/or reagents, e.g., additional components and/or reagents that may be releasable into monodisperse droplets as described herein. Template particles may include a polymer, e.g., a hydrogel. Template particles generally range from about 0.1 to about 1000 μm in diameter or larger dimension. In some embodiments, template particles have a diameter or largest dimension of about 1.0 μm to 1000 μm, inclusive, such as 1.0 μm to 750 μm, 1.0 μm to 500 μm, 1.0 μm to 250 μm, 1.0 μm to 200 μm, 1.0 μm to 150 μm 1.0 μm to 100 μm, 1.0 μm to 10 μm, or 1.0 μm to 5 μm, inclusive. In some embodiments, template particles have a diameter or largest dimension of about 10 μm to about 200 μm, e.g., about 10 μm to about 150 μm, about 10 μm to about 125 μm, or about 10 μm to about 100 μm.

In practicing the methods as described herein, the composition and nature of the template particles may vary. For instance, in certain aspects, the template particles may be microgel particles that are micron-scale spheres of gel matrix. In some embodiments, the microgels are composed of a hydrophilic polymer that is soluble in water, including alginate or agarose. In other embodiments, the microgels are composed of a lipophilic microgel. In other aspects, the template particles may be a hydrogel. In certain embodiments, the hydrogel is selected from naturally derived materials, synthetically derived materials and combinations thereof. Examples of hydrogels include, but are not limited to, collagen, hyaluronan, chitosan, fibrin, gelatin, alginate, agarose, chondroitin sulfate, polyacrylamide, polyethylene glycol (PEG), polyvinyl alcohol (PVA), acrylamide/bisacrylamide copolymer matrix, polyacrylamide/poly(acrylic acid) (PAA), hydroxyethyl methacrylate (HEMA), poly N-isopropylacrylamide (NIPAM), and polyanhydrides, poly(propylene fumarate) (PPF).

In some embodiments, the presently disclosed template particles further comprise materials which provide the template particles with a positive surface charge, or an increased positive surface charge. Such materials may be without limitation poly-lysine or Polyethyleneimine, or combinations thereof. This may increase the chances of association between the template particle and, for example, a cell which generally has a mostly negatively charged membrane.

Methods of the invention include using an optical control system to visualize the formation of pre-templated instant partitions. The optical control system may generally include a light source for transmitting light and a photodetector for detecting scattered light.

Any light source suitable for transmission of light into a liquid may be used for the device. For example and without limitation, the light source may be or include an argon lamp, deuterium lamp, halogen lamp, laser, light emitting diode (LED) mercury lamp, neon lamp, tungsten lamp, xenon arc lamp, xenon flash lamp, or combination of any of the aforementioned light sources.

Similarly, any photodetector suitable for detection of light transmitted from a liquid may be used. For example and without limitation, the photodetector may be or include a camera, charge-coupled device (CCD), complementary metal-oxide-semiconductor (CMOS) sensor, diode array, gaseous ionization detector, photodiode, photomultiplier tube, photoresistor, phototransistor, phototube, photovoltaic cell, pinned photodiode, quantum dot photoconductor, or quantum dot photodiode.

The holder and optical system may be movable relative to each other so that light can be transmitted to and sensed from multiple vessels or multiple chambers within a vessel. For example, in some embodiments the light source and photodetector is fixed within the device, and the holder is movable in one, two, or three dimensions to adjust the position of the liquid sample in relation to the light source and photodetector. In other embodiments, the holder is fixed within the device, and the light source and photodetector are movable in one, two, or three dimensions to adjust the position of the liquid sample in relation to the light source and photodetector. In other embodiments, both the holder and optical system are movable in one, two, or three dimensions to adjust the position of the liquid sample in relation to the light source and photodetector.

In some embodiments, the device includes a control system coupled to the shearing mechanism and the optical system. The control system directs the shearing mechanism to alter the shearing energy applied to the liquid in response to the transmitted light. The control mechanism may increase or decrease the shearing energy. The control system may direct the shearing mechanism to stop applying shearing energy to the liquid when the liquid comprises an emulsion comprising substantially monodisperse droplets.

In some embodiments, the device includes a user interface that allows interaction between the user and the device. The user interface may provide output about the sample to the user. For example, and without limitation, the user interface may provide information on the optical measurement that indicates whether the sample contains monodisperse droplets or on the duration and/or intensity of shearing forces applied. The user interface may include a display. The user interface may allow the user to provide input, such as information on the desired size or range of sizes of monodispersed droplets to be obtained by shearing or on the duration and/or intensity of shearing forces applied. The user interface may include a button, dial, keyboard, lever, switch, or touchpad.

The optical system may include multiple light sources and photodetectors. For example, when a multitube vessel or multiwell vessel is used, the optical system may have a separate light source and photodetector for each tube or well. Alternatively, or additionally, the optical system may have a separate light source and photodetector for each row of tubes or wells. In some embodiments, one light source is used in conjunction with multiple photodetectors to allow multiple measurements to be taken from a single liquid sample.

To monitor for the formation of pre-templated instant partitions, a transmitted light signal may be compared to a reference to determine whether additional shearing force should be applied to the sample to achieve monodisperse droplets. The reference may be transmitted light from a sample, e.g., the same sample or a different sample, prior to exposure of the sample to a shearing force. The reference may be transmitted light from a sample that has monodisperse droplets. The monodisperse droplets may have a defined size or range of sizes.

For example, if the first post-shearing optical measurement indicates that the emulsion contains droplets that are heterogeneous in size, the shearing and measurement steps may be repeated as many times as necessary to achieve monodisperse droplets. The decision on whether to repeat the shearing and measuring steps may rely on human input. Alternatively, or additionally, the decision may be made automatically by an algorithm. The algorithm may include predefined maximum and minimum signal intensities. Alternatively, or additionally, the maximum and minimum signal intensities may be determined via a machine-learning process.

The use of partition-templating particles to generate monodisperse droplets allows individual targets to be captured. By adjusting the concentration of targets in the starting sample in combination with the formation of droplets of uniform size, an emulsion can be produced in which all or nearly all droplets contain either zero or one target. See Makiko N. Hatori, Particle-Templated Emulsification for Microfluidics-Free Digital Biology, Anal. Chem. 2018, 90, 9813-9820, the content of which are incorporated herein by reference. Therefore, each droplet can serve as a reaction cell for performing a reaction on a single target.

Methods of the invention may include performing reactions in the monodisperse droplets formed by one or more of the steps described above. For example, and without limitation, the methods may include one or more of cell lysis, nucleic acid amplification, reverse transcription, or sequencing. Performing reactions in droplets formed according to one or more of the steps described above may include adjusting the temperature of the emulsions. For example, the methods may include heating and/or cooling the emulsions by convection heat transfer.

The methods and devices described herein are particularly amenable for use with amplification reactions. Any amplification reaction known in the art may be conducted on a released nucleic acid inside a pre-templated instant partition. Exemplary amplification techniques include polymerase chain reaction (PCR), reverse transcription-PCR, real-time PCR, quantitative real-time PCR, digital PCR (dPCR), digital emulsion PCR (dePCR), clonal PCR, amplified fragment length polymorphism PCR (AFLP PCR), allele specific PCR, assembly PCR, asymmetric PCR (in which a great excess of primers for a chosen strand is used), colony PCR, helicase-dependent amplification (HDA), Hot Start PCR, inverse PCR (IPCR), in situ PCR, long PCR (extension of DNA greater than about 5 kilobases), multiplex PCR, nested PCR (uses more than one pair of primers), single-cell PCR, touchdown PCR, loop-mediated isothermal PCR (LAMP), and nucleic acid sequence based amplification (NASBA). Other amplification schemes include: Ligase Chain Reaction, Branch DNA Amplification, Rolling Circle Amplification, Circle to Circle Amplification, SPIA amplification, Target Amplification by Capture and Ligation (TACL) amplification, and RACE amplification.

In certain embodiments, the reaction is QPCR or digital PCR. Digital PCR is an amplification reaction in which dilute samples are divided into many separate reactions. See for example, Brown et al. (U.S. Pat. Nos. 6,143,496 and 6,391,559), Vogelstein et al. (U.S. Pat. Nos. 6,440,706, 6,753,147, and 7,824,889), as well as Larson et al (U.S. patent application Ser. No. 13/026,120), Link et al. (U.S. patent application Ser. Nos. 11/803,101, 11/803,104, and 12/087,713), and Anderson et al (U.S. Pat. No. 7,041,481, which reissued as RE41,780), the content of each of which is incorporated by reference herein in its entirety. The distribution from background of target DNA molecules among the reactions follows Poisson statistics and at a terminal or limiting dilution, the vast majority of reactions contain either one or zero target DNA molecules.

Example 1

The ability of a device 601 of the invention to rapidly control sample temperature was evaluated.

Figure 7:
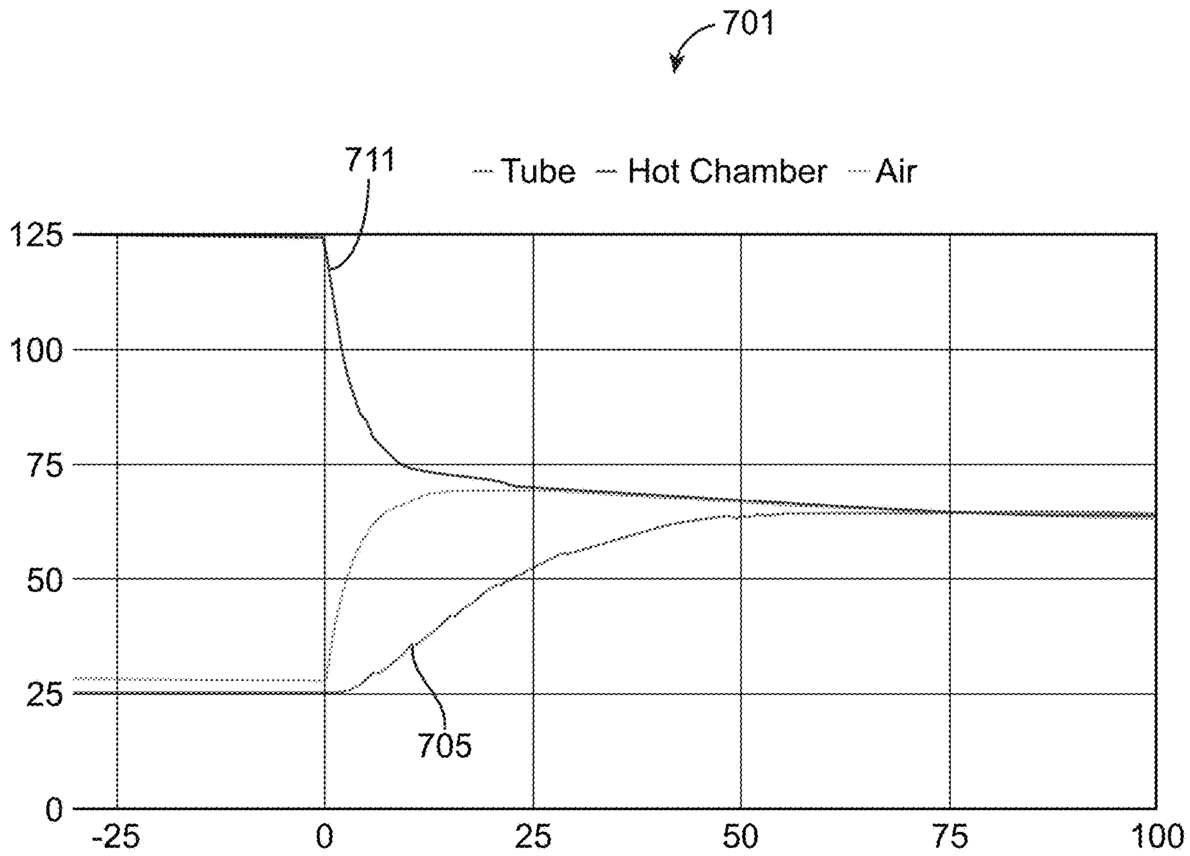
FIG. 7 shows changes in temperature over time inside a device during convective heating.

FIG. 7 shows a graph 701 demonstrating changes in temperature over time inside a device during convection heating. Shown is a graph of temperature changes collected in a tube 705 and a hot chamber 711. The Y axis of the graph corresponds with temperature in degrees Celsius. The X axis shows time in seconds. The smooth, steep slope of lines corresponding to the tube 705 and the hot chamber 711 show that devices of the invention provide for efficient, rapid changes in temperature using forced convection.

Figure 8:
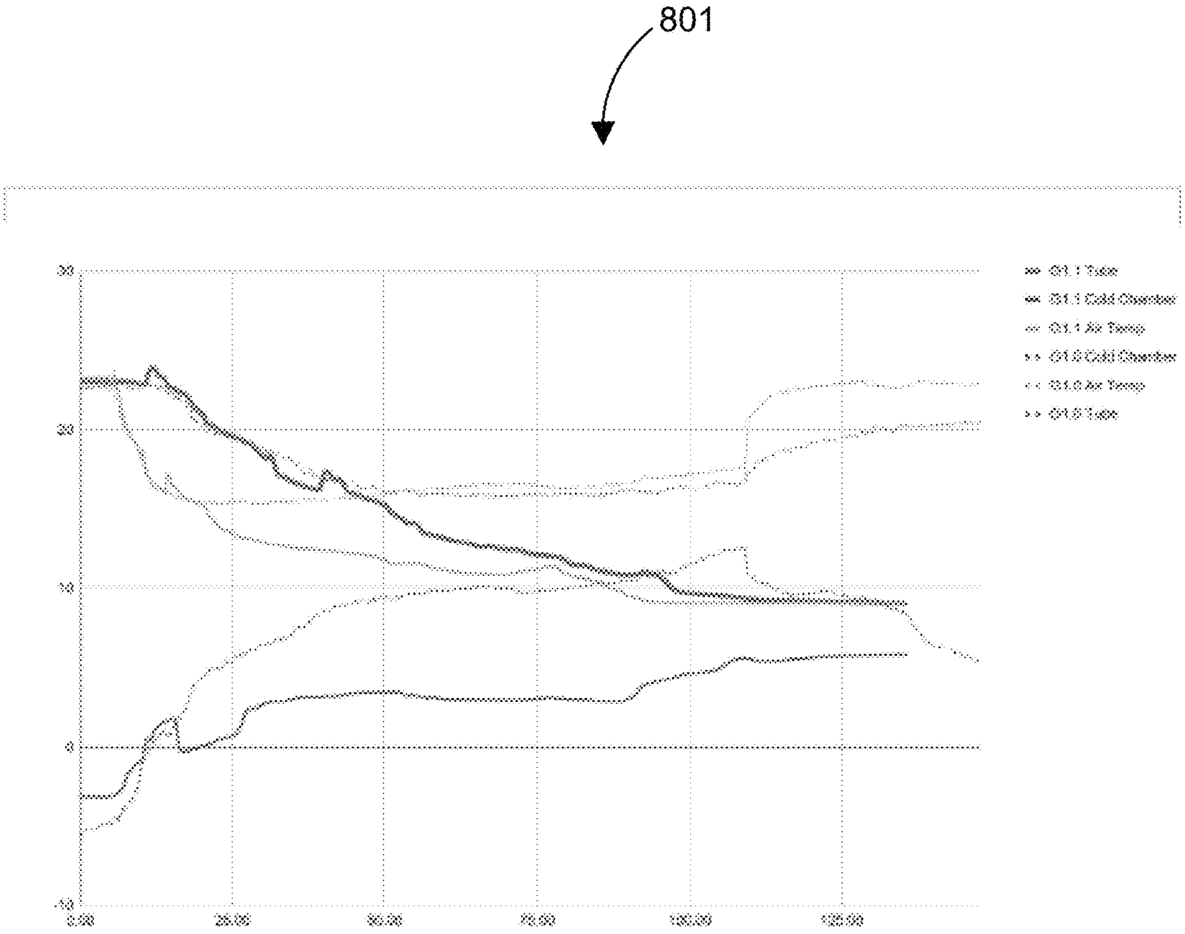
FIG. 8 shows changes in temperature over time inside a device during convective cooling.

FIG. 8 shows a graph 801 demonstrating changes in temperature over time inside a device during convection cooling.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification, and guidance that can be adapted to the practice of this invention in its various embodiments and equivalents thereof.

What is claimed is:

1. A device for generating pre-templated instant partitions, the device comprising:

a vortexer for shearing a liquid contained in at least one vessel into a plurality of pre-templated instant partitions;

a holder for securing the at least one vessel to the vortexer; and a temperature control unit operable to adjust a temperature of the liquid by convection, the temperature control unit comprising:

a first conduit for heating a fluid within the temperature control unit to a first temperature;

a second conduit for cooling the fluid to a second temperature; and a valve comprising a first position and a second position, wherein, when the valve is in the first position, fluid is blocked from flowing through the first conduit, and wherein, when the valve is in the second position, fluid is blocked from flowing through the second conduit.

2. The device of claim 1, wherein the holder comprises a clamp that can accommodate one or more vessels of different sizes or shapes.

3. The device of claim 1, wherein the holder is operable to hold the at least one vessel in a substantially vertical position while the vortexer shears the liquid.

4. The device of claim 1, wherein the holder is operable to move between securing the at least one vessel in a substantially horizontal position and a substantially vertical position while the vortexer shears the liquid.

5. The device of claim 1, wherein the vortexer is operable to shear the liquid by vortexing the at least one vessel at a speed of at least 5,000 revolutions per minute.

6. The device of claim 1, wherein the device further comprises an optical system, the optical system comprising:

a light source positioned to transmit light into the at least one vessel; and a photodetector positioned to sense light from the liquid contained in the at least one vessel.

7. The device of claim 6, further comprising a control system coupled to the vortexer and the optical system.

8. The device of claim 7, wherein the control system controls a speed of the vortexer to alter a shearing energy applied to the at least one vessel in response to the transmitted light.

9. The device of claim 8, wherein the control system directs the vortexer to stop applying the shearing energy to the at least one vessel when the liquid is substantially monodisperse.

10. The device of claim 1, wherein the device comprises at least one component manufactured by 3D printing.

11. A method for generating pre-templated instant partitions, the method comprising:

contacting at least one vessel containing a liquid with a device comprising:

a vortexer;

a holder configured to secure the at least one vessel to the vortexer; and a temperature control unit in fluidic communication with the holder, the temperature control unit comprising:

a first conduit for heating a fluid within the temperature control unit to a first temperature;

a second conduit for cooling the fluid to a second temperature; and a valve comprising a first position and a second position, wherein, when the valve is in the first position, fluid is blocked from flowing through the first conduit, and wherein, when the valve is in the second position, fluid is blocked from flowing through the second conduit;

operating the device to shear the liquid inside the at least one vessel into a plurality of pre- templated instant partitions, wherein each of the plurality of pre-templated instant partitions comprises one or zero analyte; and heating, with the temperature control unit, the at least one vessel by convection.

12. The method of claim 11, further comprising vortexing the liquid at a speed of about 5,000 revolutions per minute.

13. The method of claim 11, further comprising providing a fluid of a predetermined temperature to the holder via a first conduit.

14. The method of claim 13, further comprising providing, to the holder, a second fluid of a second predetermined temperature via a second conduit.

15. The method of claim 14, further comprising processing analyte inside the one or more of the pre-templated instant partitions by providing the first fluid to the holder thereby heating the at least one vessel.

16. The method of claim 11, further comprising:

transmitting a light to the liquid in the at least one vessel; and sensing the transmitted light from the liquid in the at least one vessel.

17. The method of claim 16, further comprising:

comparing the transmitted light from the liquid in the at least one vessel to a reference; and adjusting a speed of the vortexer in response to the comparison.

* * * * *